US00PP37261P2

(12) United States Plant Patent
Knoblauch

(10) Patent No.: US PP37,261 P2
(45) Date of Patent: Feb. 10, 2026

(54) ***BEGONIA* PLANT NAMED 'BEYZ0007'**

(50) Latin Name: *Begonia hybrida*
Varietal Denomination: BEYZ0007

(71) Applicant: SYNGENTA CROP PROTECTION AG, Basel (CH)

(72) Inventor: Cathy Knoblauch, Whitecourt (CA)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/307,610

(22) Filed: Aug. 22, 2025

(51) Int. Cl.
*A01H 5/02* (2018.01)

(52) U.S. Cl.
USPC ..... Plt./348

(58) Field of Classification Search
USPC ..... Plt./348
CPC ..... A01H 6/185; A01H 5/02
See application file for complete search history.

*Primary Examiner* — Keith O. Robinson
(74) *Attorney, Agent, or Firm* — Dale Skalla

(57) ABSTRACT

A new *Begonia* plant named 'BEYZ0007' having compact, symmetrical branching, double coral pink flowers that bloom naturally from spring to fall and has dark mahogany foliage with bright green veins.

1 Drawing Sheet

Botanical designation: *Begonia hybrida.*
Cultivar denomination: 'BEYZ0007'.

BACKGROUND OF THE NEW PLANT

The present invention comprises a new *Begonia* plant, botanically known as *Begonia hybrida,* and hereinafter referred to by the variety name 'BEYZ0007'.

'BEYZ0007' is a product of a planned breeding program in Whitecourt, Alberta, Canada The new cultivar has compact, symmetrical branching, double coral pink flowers that bloom naturally from spring to fall and has dark mahogany foliage with bright green veins.

The new *Begonia* cultivar is the result of a planned pollination made in 2021 in the inventor's nursery in Whitecourt, Alberta, Canada.

The female parent of the new cultivar is an unnamed seedling of proprietary origin, characterized by its bright pink flowers and green leaves. 'BEYZ0007' differs from the unnamed female parent by having a fuller, self-branching habit, lighter coral pink flowers and dark mahogany foliage with green veins.

The male parent of the new cultivar is an unnamed seedling of proprietary origin and differs from 'BEYZ0007' by having a more symmetrical habit and white flowers.

The resulting seed was sown in a controlled greenhouse environment in Whitecourt, Alberta and 'BEYZ0007' was selected as one flowering plant within the progeny of the stated cross in summer of 2021.

The first act of asexual reproduction of 'BEYZ0007' was accomplished when vegetative stem cuttings were propagated from the initial selection in 2021 in Whitecourt, Alberta, Canada.

BRIEF SUMMARY OF INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

A Plant Breeder's Right for this cultivar has not yet been applied for. 'BEYZ0007'has not been made publicly available prior to the effective filing date of this application, notwithstanding any disclosure that may have been made less than one year prior to the effective filing date of this application by the inventor or another who obtained 'BEYZ0007' directly from the inventor.

The following traits have been repeatedly observed and are determined to be basic characteristics of the new variety. The combination of these characteristics distinguishes this *Begonia* as a new and distinct variety.

BRIEF DESCRIPTION OF THE PHOTOGRAPHS

The accompanying photographic drawings show typical flower and foliage characteristics of 'BEYZ0007' with colors being as true as possible with an illustration of this type.

Figure 1:
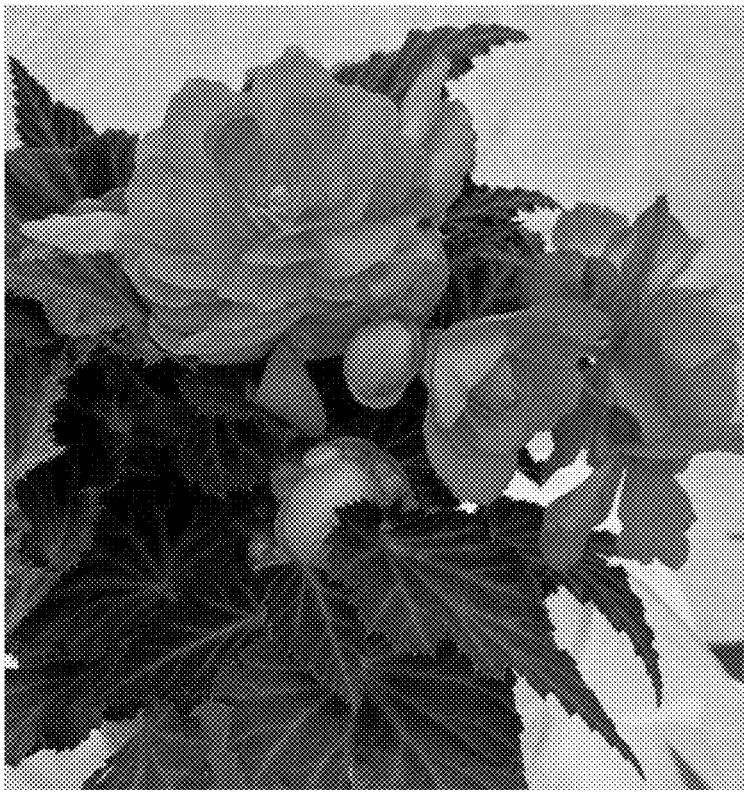
Figure 2:
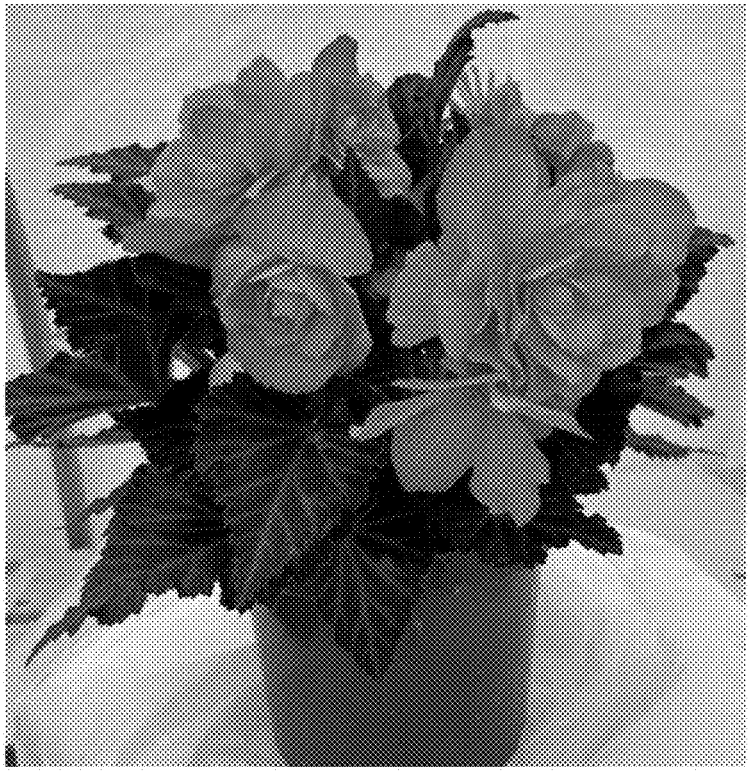

The photographic drawings show in FIG. 1 a close view of an inflorescence taken when the plants were 5 months old in August 2025 in Whitecourt, Alberta, Canada and in FIG. 2 a whole flowering plant taken in August 2025 in Whitecourt, Alberta, Canada.

DETAILED BOTANICAL DESCRIPTION

The plant descriptions and measurements were taken in August 2025 in the inventor's nursery at Whitecourt, Alberta, Canada. The plants were approximately 5 months old and were growing in 8-inch pots, one plant per pot, in a greenhouse.

Color references are made to The Royal Horticultural Society Colour Chart (R.H.S.) 2001.

TABLE 1

DIFFERENCES BETWEEN THE NEW VARIETY AND A MOST SIMILAR VARIETY

| Traits | 'BEYZ0007' | Nonstop ® Mocca Pink, Not patented |
|---|---|---|
| Flowers and leaf size: | Larger | Smaller |
| Flower color: | Soft coral pink | Bright pink |
| Foliage and branching: | Symmetrical and self-branching | Asymmetrical and slow branching |

Propagation:
- *Type*.—Vegetative tip cuttings.
- *Time to initiate roots, summer and winter*.—10-15 days.
- *Time to produce a rooted young plant summer*.—About 30 days.
- *Time to produce a rooted young plant, winter*.—About 40 days.
- *Root description*.—Fibrous, branching.
- *Rooting habit*.—Moderately free branching.

Plant description:
- *Plant and growth habit*.—Upright, mounded and freely branching.
- *Plant height, soil level to top of foliar plane*.—About 22 cm.
- *Plant height, soil level to top of floral plane*.—About 25 cm.
- *Plant width*.—About 28 cm.
- *Lateral branch description*.—Upright, branching.
- *Length*.—About 18 cm.
- *Diameter*.—About 1 cm.
- *Internode length*.—About 2 cm.
- *Strength*.—Moderately strong.
- *Aspect*.—Upright, symmetrical.
- *Texture and luster*.—Smooth, glossy.
- *Color, developing*.—Nearest RHS 171A through RHS 180A.
- *Color, developed*.—Nearest RHS 197C through RHS 199C.

Leaf description:
- *Arrangement*.—Alternate.
- *Length*.—About 10 cm.
- *Width*.—About 6 cm.
- *Shape*.—Lanceolate.
- *Apex*.—Sharply acute.
- *Base*.—Cordate.
- *Margin*.—Double serrate.
- *Texture and luster, upper and lower surfaces*.—Smooth, semi-glossy.
- *Venation pattern*.—Pinnate.
- *Developing leaves, upper surface*.—Pinnate.
- *Developing leaves, lower surface*.—Pinnate.
- *Fully expanded leaves, upper surface*.—Pinnate.
- *Fully expanded leaves, lower surface*.—Pinnate.
- *Color, upper surface, developing*.—Nearest 136A.
- *Color, lower surface, developing*.—Nearest 61A.
- *Color, upper surface, developed*.—Nearest 136A.
- *Color, lower surface, developed*.—Nearest 71A.

Petioles:
- *Length*.—About 3-5 cm.
- *Diameter*.—About 5 mm.
- *Texture and luster, upper and lower surfaces*.—Pilose, glossy.
- *Strength*.—Moderately strong.
- *Color, upper surface*.—Nearest RHS 131A.
- *Color, lower surface*.—Nearest RHS 176B to RHS 178B.

Stipules:
- *Quantity per leaf*.—2.
- *Length*.—About 1 cm.
- *Width*.—About 8 mm.
- *Shape*.—Triangular.
- *Apex*.—Roundly acute.
- *Base*.—Truncate.
- *Margins*.—Denticulate.
- *Color, upper and lower surfaces*.—Nearest RHS 146D.

Flower description:
- *Flowering habit*.—Continuous.
- *Fragrance*.—Moderately strong citrus/rose.
- *Natural flowering season*.—Spring to fall.
- *Flower longevity*.—About 30 days.
- *Inflorescence height* (*including peduncle*).—About 8 cm.
- *Flower buds, female flowers*.—
- *Length*.—About 3 cm.
- *Diameter, flattened*.—About 2.5 cm.
- *Shape*.—Broadly ovate.
- *Texture and luster*.—Smooth, matte.
- *Color, upper surface*.—Nearest RHS 38B.
- *Color, lower surface*.—: Nearest RHS 38C.
- *Flower buds, male flowers*.—
- *Length*.—About 3 cm.
- *Diameter, flattened*.—About 4 cm.
- *Shape*.—Broadly ovate.
- *Texture and luster*.—Smooth, matte.
- *Color, upper surface*.—Nearest RHS 145D through RHS 37B.
- *Color, lower surface*.—Nearest RHS 149D through RHS 39C.
- *Female flowers size*.—
- *Length About* 8 cm.
- *Depth*.—About 9 cm.

Tepals, female flowers:
- *Quantity per flower and arrangement*.—5 arranged in a single whorl.
- *Shape, tepals*.—Ovate.
- *Length, tepals*.—About 2 cm.
- *Width, tepals*.—About 3 cm. One single whorl of petals.
- *Apex, female tepals*.—Roundly obtuse. There are no outer tepals, there is only one whorl of petals.
- *Base, female tepals*.—Obtuse.
- *Margin, female tepals*.—Entire.
- *Texture and luster, female tepals, upper surface*.—Smooth, matte.
- *Texture and luster, female tepals, lower surface*.—Smooth, matte.
- *Color, female tepals*.—There are no inner or outer tepals. Just one whorl of which the colors are described below.
- *Color, outer tepals*.—
- *When opening, upper surface*.—Nearest RHS 19B.
- *When opening, lower surface*.—Nearest RHS 27B.
- *Fully opened, upper surface*.—Nearest RHS 31D.
- *Fully opened, lower surface*.—Nearest RHS 37C.
- *Tepaloids*.—None observed on female flowers.

Male flowers:
- *Size*.—Width: About 10 cm.
- *Depth*.—Length: About 9 cm.

Tepals, male flowers:
*Quantity per flower and arrangement*.—About 35 to 30 arranged in about 8 whorls.
Male flowers:
*Length, inner tepals*.—About 3 cm.
*Length, outer tepals*.—About 5 cm.
*Width, inner tepals*.—About 2 cm.
*Width, outer tepals*.—About 5 cm.
*Shape, inner tepals*.—Obovate.
*Shape, outer tepals*.—Broadly ovate.
*Apex, inner and outer tepals*.—Roundly acute.
*Base, inner tepal*.—Acute.
*Base, outer tepal*.—Obtuse.
*Margin, inner and outer tepals*.—Entire.
*Texture and luster, inner and outer tepals, upper surface*.—Smooth, matte.
*Texture and luster, inner and outer tepals, lower surface*.—Smooth, matte.
*Color, inner tepals*.—
*When opening, upper surface*.—Nearest RHS 160A through RHS 33D.
*When opening, lower surface*.—Nearest RHS 19D through RHS 33D.
*Fully opened, upper and lower surfaces*.—Nearest RHS 160A through RHS 33D.
*Color, outer tepals*.—
*When opening, upper surface*.—Nearest RHS 23C through RHS 33C.
*When opening, lower surface*.—Nearest RHS 18C through RHS 33D.
*Fully opened, upper surface*.—Nearest RHS 17D through RHS 33B.
*Fully opened, lower surface*.—Nearest RHS 18A through RHS 34B.
*Tepaloids*.—None observed on male flowers.
Peduncles:
*Length*.—About 9 cm.
*Diameter*.—About 5 mm.
*Angle*.—Acute.
*Strength*.—Moderate.
*Texture and luster*.—Pilose, semi glossy.
*Color, upper and lower surfaces*.—Upper, nearest RHS 35B, Lower, nearest RHS 28D.
Pedicels, female flowers:
*Length*.—About 4 cm.
*Diameter*.—About 3 mm.
*Angle*.—Reflex.
*Strength*.—Moderate.
*Texture and luster*.—Pilose, semi-glossy.
*Color, upper surface*.—Nearest RHS 31B.
*Color, lower surface*.—Nearest RHS 29B.
Pedicels, male flowers:
*Length*.—About 2 cm.
*Diameter*.—About 3 mm.
*Angle*.—Straight.
*Strength*.—Moderate.
*Texture and luster*.—Pilose, semi-glossy.
*Color, upper surface*.—Nearest to RHS 26B.
*Color, lower surface*.—Nearest to RHS 16D.
FLOWER BRACTS
*Quantity per flower and arrangement*.—2, opposite.
*Length*.—About 1.5 cm.
*Width*.—About 1.5 cm.
*Shape*.—Broadly ovate.
*Apex*.—Roundly obtuse.
*Base*.—Obtuse.
*Margin*.—Entire, ciliate.
*Texture and luster, upper and lower surfaces*.—Smooth, semi gloss semi-glossy.
*Color, upper and lower surfaces*.—Nearest RHS 194B.
REPRODUCTIVE ORGANS
*Androecium*.—
*Stamen quantity per flower*.—None.
*Filament length*.—None.
*Filament color*.—None.
*Anther size*.—None.
*Anther shape*.—None.
*Anther color*.—None.
*Amount of pollen*.—None.
*Pollen color*.—None.
*Gynoecium*.—
*Quantity per flower*.—One.
*Pistil length*.—About 1 mm.
*Stigma diameter*.—About 5 mm.
*Stigma shape*.—Double spiral.
*Stigma color*.—Nearest RHS 3B.
*Style length*.—About 1 mm.
*Style color*.—Nearest RHS 3D.
*Ovary color*.—Nearest RHS 144B.
*Seeds and fruits*.—None observed.
Pathogen & pest resistance: To date, resistance to pathogens and pests common to *Begonia* plants has not been observed on plants of the new *Begonia*.
Temperature tolerance: Plants of the new *Begonia* have been observed to tolerate high temperatures of about 30° C. and to be suitable for USDA Hardiness Zones 7 to 9.

What is claimed is:

1. A new and distinct variety of *Begonia* plant named 'BEYZ0007' substantially as illustrated and described herein.

* * * * *